US 7,818,076 B2

(12) United States Patent
Viswanathan

(10) Patent No.: US 7,818,076 B2
(45) Date of Patent: Oct. 19, 2010

(54) METHOD AND APPARATUS FOR MULTI-SYSTEM REMOTE SURGICAL NAVIGATION FROM A SINGLE CONTROL CENTER

(75) Inventor: Raju R. Viswanathan, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 923 days.

(21) Appl. No.: 11/672,358

(22) Filed: Feb. 7, 2007

(65) Prior Publication Data
US 2007/0197901 A1 Aug. 23, 2007

Related U.S. Application Data

(63) Continuation-in-part of application No. 11/484,883, filed on Jul. 11, 2006, now abandoned.

(60) Provisional application No. 60/702,486, filed on Jul. 26, 2005.

(51) Int. Cl.
G06F 17/00 (2006.01)
G05B 19/18 (2006.01)
G08B 1/08 (2006.01)
A61B 5/00 (2006.01)
A61B 3/16 (2006.01)

(52) U.S. Cl. .............. 700/90; 700/65; 340/539.12; 600/300; 600/411

(58) Field of Classification Search .............. 700/65, 700/90; 600/300, 411, 424; 340/539.12
See application file for complete search history.

(56) References Cited

U.S. PATENT DOCUMENTS

| | | | |
|---|---|---|---|
| 5,654,864 A | 8/1997 | Ritter et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |

(Continued)

*Primary Examiner*—Ramesh B Patel
(74) *Attorney, Agent, or Firm*—Harness, Dickey & Pierce, P.L.C.

(57) ABSTRACT

A system and method are provided for performing remote surgical navigation in multiple systems from a single control center, where there are at least two remote navigation systems in separate procedure rooms having respective control computers. The system includes a Control Center separate from each procedure room that has a set of displays and interface input devices. A switch may also be included for connecting the Control Center to the set of displays, interface input devices, and remote navigation systems. A method is provided for performing multiple simultaneous remote medical procedures that includes displaying information transmitted from a remote navigation system to the Control Center, and accepting user input from a remote navigation system. The method provides for establishing an encryption key with the remote system, converting the user input to a script data and encrypting the data. The transmitted script command is then transmitted to the remote navigation system.

11 Claims, 2 Drawing Sheets

U.S. PATENT DOCUMENTS

| | | |
|---|---|---|
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,480,745 B2 * | 11/2002 | Nelson et al. .................. 607/60 |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,574,239 B1 * | 6/2003 | Dowling et al. ............. 370/469 |
| 6,630,879 B1 | 10/2003 | Creighton, IV et al. |
| 6,650,932 B1 * | 11/2003 | Menzie et al. .............. 600/513 |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 6,980,958 B1 * | 12/2005 | Surwit et al. .................... 705/2 |
| 7,008,418 B2 | 3/2006 | Hall et al. |
| 7,010,338 B2 | 3/2006 | Ritter et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,088,233 B2 * | 8/2006 | Menard ................... 340/539.1 |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 2001/0031998 A1 * | 10/2001 | Nelson et al. .................. 607/60 |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2002/0177789 A1 | 11/2002 | Ferry et al. |
| 2003/0036683 A1 * | 2/2003 | Kehr et al. .................. 600/300 |
| 2003/0125752 A1 | 7/2003 | Werp et al. |
| 2003/0153818 A1 * | 8/2003 | Bocionek et al. ............ 600/300 |
| 2003/0185195 A1 * | 10/2003 | Dowling et al. ............. 370/349 |
| 2004/0002643 A1 | 1/2004 | Hastings et al. |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0199074 A1 | 10/2004 | Ritter et al. |
| 2004/0235469 A1 * | 11/2004 | Krug .......................... 455/431 |
| 2004/0246128 A1 * | 12/2004 | Menard ................. 340/539.19 |
| 2004/0249262 A1 | 12/2004 | Werp et al. |
| 2004/0249263 A1 | 12/2004 | Creighton, IV |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 * | 1/2005 | Viswanathan et al. ....... 600/424 |
| 2005/0021063 A1 | 1/2005 | Hall et al. |
| 2005/0033162 A1 | 2/2005 | Garibaldi et al. |
| 2005/0043611 A1 | 2/2005 | Sabo et al. |
| 2005/0065435 A1 * | 3/2005 | Rauch et al. ................. 600/427 |
| 2005/0096589 A1 | 5/2005 | Shachar |
| 2005/0113628 A1 | 5/2005 | Creighton, IV et al. |
| 2005/0113812 A1 * | 5/2005 | Viswanathan et al. .......... 606/1 |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 * | 11/2005 | Hastings et al. ............. 600/423 |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 * | 2/2006 | Viswanathan et al. ....... 600/424 |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 * | 2/2006 | Viswanathan et al. ......... 600/11 |
| 2006/0041245 A1 | 2/2006 | Ferry et al. |
| 2006/0058646 A1 | 3/2006 | Viswanathan |
| 2006/0061445 A1 | 3/2006 | Creighton, IV et al. |
| 2006/0074297 A1 | 4/2006 | Viswanathan |
| 2006/0079745 A1 * | 4/2006 | Viswanathan ............... 600/407 |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0145799 A1 | 7/2006 | Creighton, IV |
| 2006/0154642 A1 * | 7/2006 | Scannell, Jr. ............. 455/404.1 |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0016010 A1 | 1/2007 | Creighton, IV et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0030958 A1 | 2/2007 | Munger |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 * | 2/2007 | Viswanathan .......... 340/539.12 |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0088197 A1 | 4/2007 | Garibaldi et al. |
| 2008/0055239 A1 * | 3/2008 | Garibaldi et al. ............ 345/156 |
| 2008/0058609 A1 * | 3/2008 | Garibaldi et al. ............ 600/300 |
| 2008/0058963 A1 * | 3/2008 | Garibaldi et al. .............. 700/19 |

* cited by examiner

METHOD AND APPARATUS FOR MULTI-SYSTEM REMOTE SURGICAL NAVIGATION FROM A SINGLE CONTROL CENTER

CROSS-REFERENCE TO RELATED APPLICATIONS

This application is a continuation-in-part of U.S. patent application Ser. No. 11/484,883, filed Jul. 11, 2006, which application claims the benefit of U.S. Provisional Patent Application Ser. No. 60/702,486, filed Jul. 26, 2005, the entire disclosure of which is incorporated herein by reference.

FIELD

The present invention relates to the medical procedures which utilize navigation of medical devices within a subject body, and more specifically to remotely performing medical procedures utilizing navigation of medical devices in a subject body.

BACKGROUND

Navigation systems have been commercially developed recently for actuation of medical devices to be steered within a patient's anatomy, from a remote location nearby the patient. An example is the Niobe magnetic navigation system developed and sold by Stereotaxis, Inc. Such a system typically allows for control of the navigation of a minimally interventional device with the help of a Graphical User Interface and user input devices such as a mouse, keyboard, joystick or other form of interface input device.

While the use of such a remote navigation system can bring higher efficiencies to the Catheter Lab where it is installed, at centers where a larger volume of cases are typically performed, it is advantageous to install and use more than one remote navigation system. However, controls for each navigation system are costly, and a physician with significant expertise in such systems may not be available for every navigation system and patient.

SUMMARY

The present invention describes methods and apparatus details for the functioning of a Control Center from which multiple remote navigation systems could be controlled simultaneously or nearly simultaneously. The ability to perform multiple procedures simultaneously from a single integrated Control Center is advantageous. There are significant potential benefits in terms of cost and time savings with such a single Control Center. Likewise, an expert physician could control and perform a procedure at a distant site, possibly thousands of kilometers away, or even at multiple distant sites, from such an integrated Control Center. Such a scenario will result in cost and time savings, as well as expert care for a patient who might otherwise not have access to suitable expert physicians.

In accordance with one aspect of the invention, various embodiments are provided of a system for performing remote surgical navigation in multiple systems from a single control center, where there are at least two remote navigation systems in separate procedure rooms. The at least two remote navigation systems each include respective control computers. The system further includes a Control Center that is physically separated by at least 5 meters from each procedure room, the Control Center having a set of displays and interface input devices. A switch may also be included for connecting the set of displays and interface input devices to the Control Center, and also for connecting to each of aforesaid remote navigation systems by means of communication links. The switch may include user-selectable settings for selecting and routing interaction between the set of displays and interface input devices and any one of the remote navigation systems.

In another aspect of the present invention, one embodiment of a method is provided for performing multiple simultaneous remote medical interventional procedures on any of a set of remote navigation systems from a single, physically distant Control Center. The method includes the step of displaying information that is transmitted over a link from any of the remote navigation systems to the Control Center. The method also includes receiving or accepting user input into the Control Center computer, and establishing an encryption key between the Control Center computer and the remote navigation system computer. The Control Center converts the user input data to a pre-determined data stream format, and then encrypts this data on the Control Center computer. The Control Center further transmits the encrypted data over a link from the Control Center computer to a computer at the remote navigation system site. The transmitted data received by the remote systems is then decrypted and converted to a set of pre-determined script commands corresponding to medical device control and user interaction elements. The decrypted pre-determined script commands may then be transmitted to the remote navigation system control computer via a local, standard Ethernet link. Alternatively, the script commands may be transmitted to the remote navigation system control computer via a local, standard USB cable link.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
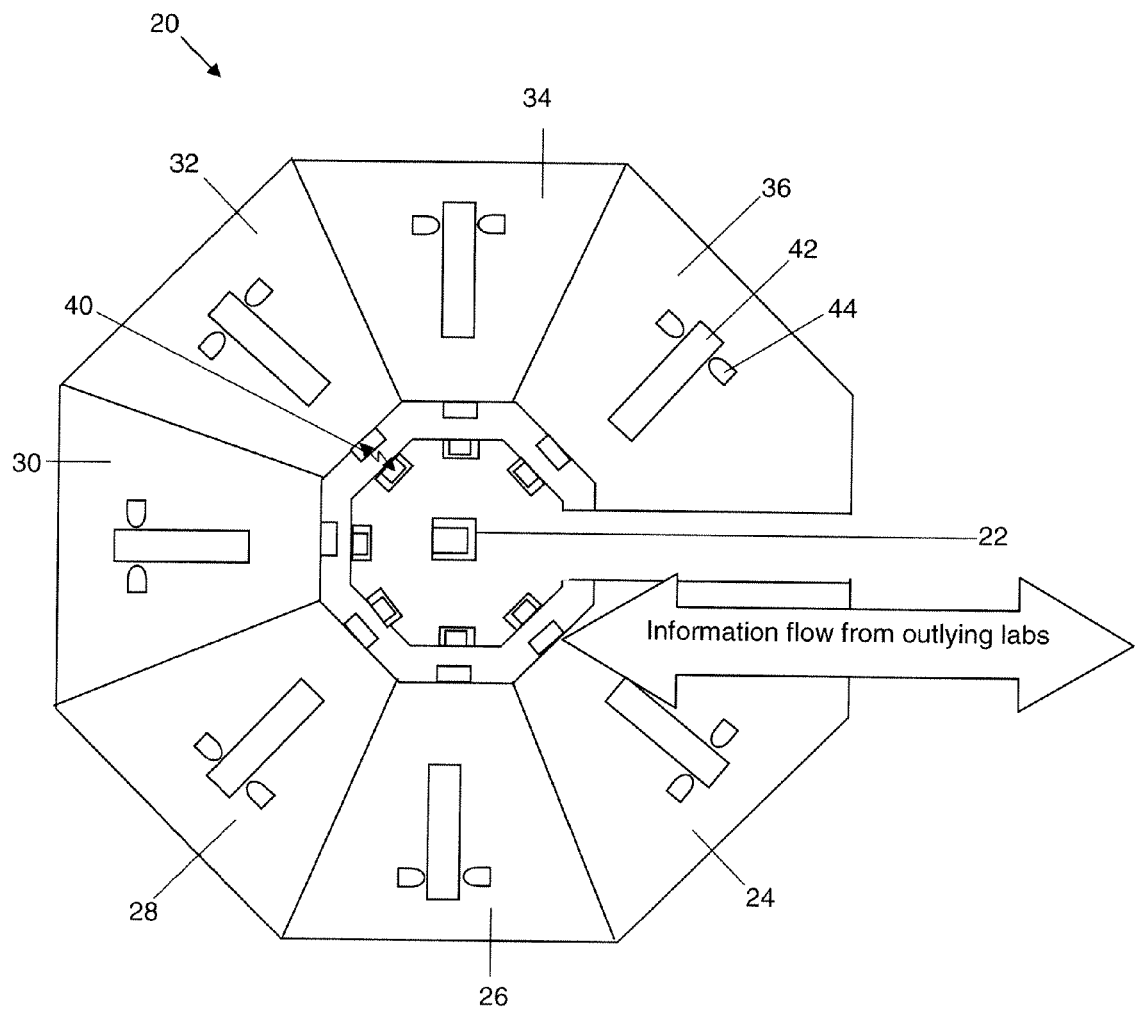
FIG. 1 shows a schematic of a Multi-System Control Center capable of linking to remote location sites.

The following description of the various embodiments is merely exemplary in nature and is in no way intended to limit the invention, its application, or uses.

In some embodiments, each remote navigation system is installed in its own procedure room. At sites where there are multiple such systems at the same clinical facility, other embodiments comprise remote navigation systems that are installed in adjacent rooms so that economies of scale could result in net installation costs that are lower. In one embodiment, a system is provided for performing multiple simultaneous remote medical interventional procedures from a single Control Center where at least two remote navigation systems are included. The at least two remote navigation systems are in separate procedure rooms, and have respective control computers for each remote navigation system. The system includes a Control Center that is physically separated by at least 5 meters from each procedure room. The Control Center has a set of at least one display and at least one interface input device corresponding to each of aforesaid remote navigation systems that are respectively connected to the respective control computers of the remote navigation systems by means of corresponding communication links. The system may further include a switch connected to the set of displays and interface input devices in the Control Center. The switch is also connected to each of aforesaid remote navigation systems by means of communication links, and has user-selectable settings for selecting and routing interaction between the set of displays and interface input devices and any one of the remote navigation systems. The communication link in the system may be a physical connection that comprises optical fibers, or alternatively copper conductors. The communication link may also be a wireless connection, and may employ a portion of the electromagnetic spectrum of the individual navigation systems for establishing wireless communication.

In some embodiments, the switch of the system may also accept inputs from audio channels for each remote navigation system, to provide for two-way audio communication between the Control Center and each procedure room. System selection on the switch unit automatically routes the two-way audio signals from the appropriate procedure room to the Control Center. The system may further include a means to indicate that communication is awaited by a procedure room different from the one currently selected is passed along to the user.

The switch connecting the set of interface input devices to the Control Center also enables the Control Center to provide master/slave arrangement for control of various remote navigation systems. For example, where a procedure is being performed on a patient at a remote navigation system by a physician at the remote navigation system, a physician at the Control Center may monitor the procedure being performed at the remote navigation system, and even participate. From the Control Center, a physician possessing expertise with such navigation systems can monitor several procedures being performed remotely at several remote navigation systems. The Control Center may be configured to receive user input data from each remote navigation system through the switch, and to convert the data stream to a set of pre-determined script commands corresponding to medical device control for the each remote navigation system. The Control Center may also comprise a local user interface means for controlling a remote navigation system, where the Control Center's interface means overrides the user input data received from the remote navigation system and provides medical device control commands to the remote navigation system. If the expert physician at the Control Center determines that a certain procedure needs his assistance, the expert physician may use interface means at the Control Center to control the remote navigation system, and override the physician at the remote navigation system. Thus, each patient at each remote navigation system can receive the benefit of an expert physician supervising the medical procedure being performed.

In one embodiment, the Control Center has one set of displays for each remote navigation system that is to be controlled from there. The different displays are set up as part of an operating console within which the physician performing the procedures sits. In addition to at least one display corresponding to each remote navigation system, there is at least one set of interface input devices (such as a computer mouse, keyboard, joystick, etc.) associated with each remote navigation system. Each interface input device is connected to its corresponding remote navigation system computer through a standard USB cable possibly by routing through at least one USB Switch unit and cable extensions if extended lengths are required due to larger physical separations. These input devices can be used to steer the medical device. FIG. 1 shows a Multi-system application 20 having a Control Center 22 from which remote navigation systems 24, 26, 28, 30, 32, 34 and 36 are controlled for performing multiple simultaneous interventional medical procedures. Each navigation system comprises a patient support 42, one or more magnetic field sources 44, and other user input and navigational display consoles for use by a physician. One or more of these remote systems could be distant from the Control Center. Systems 22-34 are connected to displays and interface input devices 24-36 in the Control Center by means of links 40.

In the case of a magnetic navigation system, a magnetic field can be directed suitably and applied to steer the device. In the case of a mechanical remote navigation system, the tension in various pull wires can be controlled or various servo motors can be controlled to suitably actuate and steer the device. Other schemes of remote actuation are familiar to those skilled in the art and the teachings here apply to any such remote actuation scheme.

In an alternate, second embodiment, the Control Center employs a single set of displays and interface input devices. In this case, a switch unit for system selection, possibly specially customized, is used by the user to select the remote navigation system that the user currently desires to control. The switch unit for system selection has a knob or sliding bar control and a set of markings labeling the different remote navigation systems connected to it. The interface input devices are connected to the switch unit for system selection. Given a particular system selection set by the user, the switch unit routes the inputs from the set of interface input devices to that particular remote navigation system computer through a suitable USB cable connection. Likewise, the various system displays feed into the switch unit for system selection. Depending on the system selected, the corresponding data for the set of displays of the selected remote navigation system are fed on to the actual set of displays in the Control Center. Thus in this embodiment, the user works from a single set of displays and directly controls the remote navigation system that he/she has currently selected. Clutter in the Control Center is thereby reduced in this embodiment since there is only a single set of displays and interface input devices.

In a third embodiment that augments the first embodiment, audio data from the procedure rooms also feed into as many speakers and microphones in the Control Center for two-way audio communication. The microphone in the Control Center that is associated with each remote navigation system is endowed with a button so that the user can choose to speak into the microphone for a given remote navigation system for purposes of verbally addressing the corresponding procedure room.

In a fourth embodiment that augments the second embodiment with a single set of displays, the switch unit for system selection also accepts inputs from the audio channels for each remote navigation system. System selection on the switch unit automatically routes the two-way audio signals from the appropriate procedure room to the Control Center. In this manner, two-way audio communication between the procedure room of the currently selected remote navigation system and the Control Center is established. If a different procedure room other than the one selected desires to establish audio communication (by depressing a button to indicate the corresponding microphone is enabled), the associated button press signal is detected by the switch unit for system selection and a corresponding signal is passed along as a periodic audible tone to a speaker installed in the Control Center for this purpose. Thus an indication that communication is awaited by a procedure room different from the one currently selected is passed along to the user in the Control Center.

In a fifth embodiment, in addition to some of the features in the previous embodiments described, the remote navigation system being controlled from the Control Center could be located at a distant and distinct clinical site. In this case, a dedicated cable channel, satellite channel or a direct Copper or optical link is used to provide system command transmissions from the Control Center to the remote/distant site and data, confirmation messages and display details in the reverse direction. It is desirable for safety reasons that this be a dedicated, secure link. If for technical reasons security is not guaranteed, then any data or commands that are exchanged are encrypted before being sent. In this case there is additionally a computer in the Control Center. The key for the encryption is established upon initiation of the connection between the Control Center computer and the remote navigation system computer at the distant site according to standard public key encryption protocols. Whereas previously data and commands were exchanged from the Control Center and the remote navigation system by means of USB connections, in the case of the present embodiment, USB signals are not directly exchanged. Rather, the Control Center computer converts the USB data to a pre-determined data stream format before encryption and transmission as system commands. The data is received by a reception computer at the remote navigation system site that could be one of the existing remote navigation system computers, or an additional one that exists to accept the incoming encrypted data, decrypts the data, converts the data from the pre-determined data stream format to USB data (thereby functioning as an USB emulator), and then passes it on to the remote navigation system control computer at the distant site via a local, standard USB cable link. In this manner the commands are again provided as standard system interface inputs such as joystick movements, mouse click events at a particular location on the GUI, etc. at the distant site.

In a sixth embodiment, the data from the reception computer could, instead of being converted to USB data, be sent to the remote navigation system control computer in the form of script commands that execute certain processes on the latter that serve to implement the desired user actions in order to control the remote navigation system and the medical device used in the procedure. Such actions could include, for instance in the case of a magnetic navigation system, clicking on a GUI to change external magnetic fields, advance or retract the device, mark anatomical reference locations. In the case of a mechanically actuated remote navigation system, these actions could include requesting actuations that increase or decrease deflection of the medical device, advance or retract a medical device, and other typical catheter manipulations.

Figure 2:
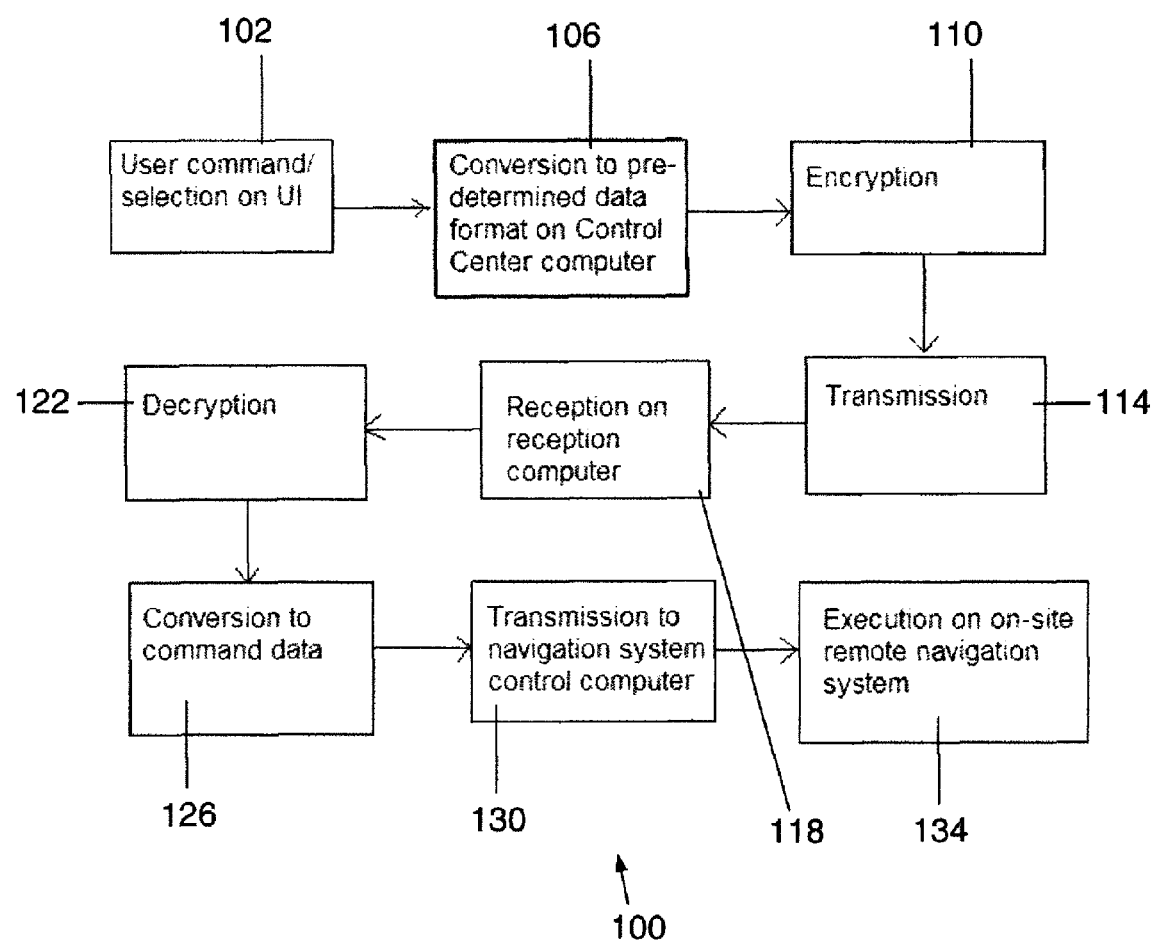
FIG. 2 shows a schematic of one embodiment of a method of command data transmission from a Multi-System Control Center for execution at an on-site remote navigation system.

FIG. 2 shows a schematic of a method of command data transmission from a Multi-System Control Center for execution at an on-site remote navigation system shown at 134. The process described in the latter two embodiments is schematically represented in this Figure. In at least one embodiment, a method is provided for performing multiple simultaneous remote medical interventional procedures on any of a set of remote navigation systems from a single, physically distant Control Center. The method includes the step of displaying information that is transmitted over a link from any of the remote navigation systems to the Control Center. The method also includes receiving or accepting user input at step 102, into the Control Center computer at step 106, and establishing an encryption key at step 110 between the Control Center computer and the remote navigation system computer 130. At step 106, the Control Center converts the user input data to a pre-determined data stream format, and then encrypts this data on the Control Center computer at step 110. At step 114, the Control Center further transmits the encrypted data over a link from the Control Center computer to a computer at the remote navigation system site. The transmitted data received by the remote systems at step 118 is then decrypted at step 122, and then converted at step 126 to a set of pre-determined script commands corresponding to medical device control and user interaction elements. The decrypted pre-determined script commands may then be transmitted at step 130 to the remote navigation system control computer via a local, standard Ethernet link. Alternatively, the script commands may be transmitted to the remote navigation system control computer via a local, standard USB cable link.

In some of the latter embodiments, the reception computer also sends data such as display data to the Control Center computer. For efficiency reasons, it would only send updates or changes to currently existing displays to the Control Center computer. Since only system commands and incremental changes to existing displays are transmitted over the dedicated/secure link, this is an efficient methodology for system communication between the Control Center and the remote navigation site and provides a good platform for real-time control of a distant remote navigation system from the Control Center, regardless of where these are located physically.

In the various embodiments, a local over-ride option at each remote navigation site is implemented as an additional safety feature in case transmission from the Control Center fails for any reason, or is intermittent, or if the clinical situation in the procedure room warrants this. The local over-ride could be implemented for instance as a fail-safe button that when pressed remains visibly depressed/pushed down, possibly including the display of messages on the User Interface indicating that local over-ride is in effect. Such messages would also be attempted to be transmitted back to the Control Center. The local over-ride would take precedence over any commands issued from the Control Center.

The above teachings clearly could be applied to a variety of remotely actuated navigation systems in interventional medicine, whether the actuation scheme is magnetic, mechanical, electrostrictive, hydraulic, or any other form familiar to those skilled in the art. Likewise, while specific embodiments are detailed above, variations and alternative embodiments dictated by convenience and ease of implementation are within the scope of the teachings contained herein, and limited only by the appended claims.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for performing multiple simultaneous remote medical interventional procedures from a single control center, the system comprising:

at least two remote navigation systems in separate procedure rooms, and respective control computers for each remote navigation system;

a control center that is physically separated by at least 5 meters from each procedure room, the control center having a set of at least one display and at least one interface input device corresponding to each aforesaid remote navigation systems, that are respectively connected to the respective control computers of the remote navigation systems by corresponding links.

2. The system of claim 1, the system including a set of audio speakers and at least one microphone in the control center for each remote having a navigation system that is connected thereto, wherein each of the at least one microphone is additionally endowed with a button so that the user can choose to verbally address the procedure room of the corresponding remote navigation system.

3. The system of claim 1, where the link is a physical connection using copper conductors.

4. The system of claim 1, where the link is a physical connection using optical fibers.

5. The system of claim 1, where the link is a wireless connection employing a portion of the electromagnetic spectrum for communication.

6. A system for performing multiple simultaneous remote medical interventional procedures from a single control center, the system comprising:
   at least two remote navigation systems in separate procedure rooms, and respective control computers;
   a control center that is physically separated by at least 5 meters from each procedure room, the control center having a set of displays and interface input devices;
   a switch connected to the set of displays and interface input devices in the control center, and also connected to each of aforesaid remote navigation systems by communication links, with user-selectable settings for selecting and routing interaction between the set of displays and interface input devices and any one of the remote navigation systems.

7. The system of claim 6, where the switch also accepts inputs from audio channels for each remote navigation system for two-way audio communication between the control center and each procedure room, and system selection on the switch unit automatically routes the two-way audio signals from the appropriate procedure room to the control center.

8. The system of claim 7, where there is a an indicator that communication is awaited by a procedure room different from the one currently selected is passed along to the user.

9. The system of claim 6, where the link is a physical connection using copper conductors.

10. The system of claim 6, where the link is a physical connection using optical fibers.

11. The system of claim 6, where the link is a wireless connection employing a portion of the electromagnetic spectrum for communication.

* * * * *